United States Patent [19]

Müllner

[11] Patent Number: 4,948,481
[45] Date of Patent: Aug. 14, 1990

[54] PROCESS AND DEVICE FOR THE ELECTROPHORETIC SEPARATION, PURIFICATION AND CONCENTRATION OF CHARGED OR POLARIZABLE MACROMOLECULES

[75] Inventor: Stefan Müllner, Frankfurt am Main, Fed. Rep. of Germany

[73] Assignee: Hoechst Aktiengesellschaft, Frankfurt am Main, Fed. Rep. of Germany

[21] Appl. No.: 398,434

[22] Filed: Aug. 25, 1989

[30] Foreign Application Priority Data

Aug. 27, 1988 [DE] Fed. Rep. of Germany ....... 3829111

[51] Int. Cl.$^5$ .............................................. C07K 3/14
[52] U.S. Cl. ............................ 204/182.8; 204/299 R
[58] Field of Search ..................... 204/182.8, 299 R

[56] References Cited

U.S. PATENT DOCUMENTS 4,441,978  4/1984  Jain ................................ 204/299 R

FOREIGN PATENT DOCUMENTS 1098307  1/1968  United Kingdom .

Primary Examiner—John F. Niebling
Assistant Examiner—David G. Ryser
Attorney, Agent, or Firm—Finnegan, Henderson, Farabow, Garrett, and Dunner

[57] ABSTRACT

In the process for the electrophoretic separation, purification and concentration of charged or polarizable macromolecules from a mixture of these molecules in a separation column with a slab or bar gel as the support, the macromolecules separated in the support are caused to migrate out of the support by means of the electrophoretic current and are fed into a multielectrode collector (13) via a molecule detector (5) and a distributor (6). Each of the electrodes of the multielectrode collector is individually activated according to a signal coming from the molecule detector (5).

13 Claims, 1 Drawing Sheet

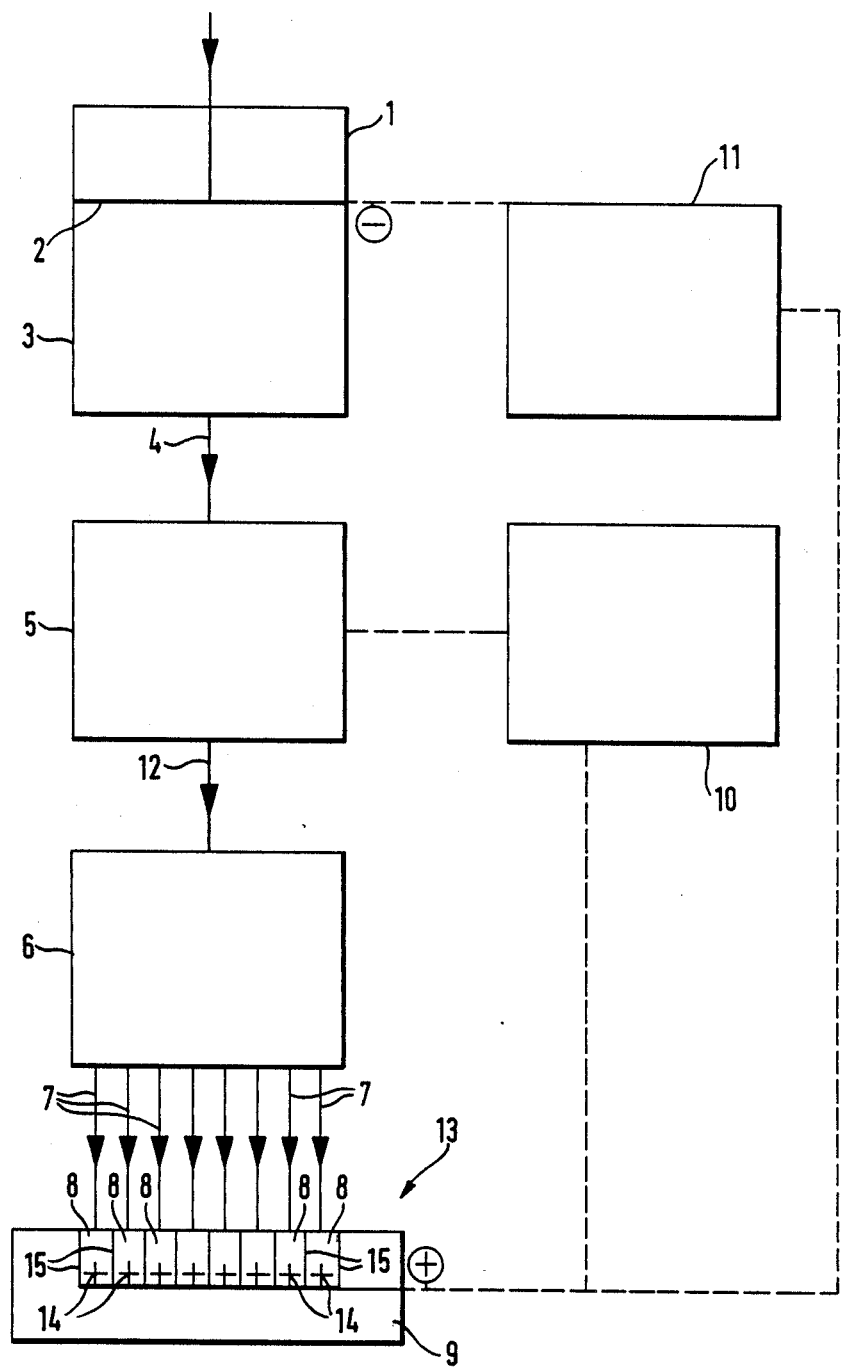

PROCESS AND DEVICE FOR THE ELECTROPHORETIC SEPARATION, PURIFICATION AND CONCENTRATION OF CHARGED OR POLARIZABLE MACROMOLECULES

DESCRIPTION

The invention relates to a process for the electrophoretic separation, purification and concentration of charged or polarizable macromolecules from a mixture of these molecules in a separation column with a slab or bar gel as the support.

The invention further relates to a device for carrying out the process.

The separation and analysis of charged macromolecules by electrophoretic methods is known, e.g. the sodium dodecylsulfate (SDS)/polyacrylamide gel electrophoresis of proteins, the denaturing polyacrylamide electrophoresis of DNA (deoxyribonucleic acid) in the presence of urea, and the electrophoresis of proteins such as immunoglobulins and of DNA/RNA in agarose gel. Various specific staining methods, radioactive isotope labeling and autoradiography are known for the direct quantification of these macromolecules. If it is possible at all, recovery of the types of macromolecule to be investigated is time-consuming and they can only be recovered in small amounts. Proteins, for example, must first be visualized under denaturing conditions, cut out of the gel and eluted, which entails considerable losses of yield.

The object of the invention is accordingly to provide a process and a device which enable electrophoretically separated macromolecules to be obtained quantitatively, i.e. without losses of yield.

The invention achieves this object, in the process of the type mentioned in the introduction, by causing the macro-molecules separated in the support to migrate out of the support by means of the electrophoretic current, feeding them into a multielectrode collector via a molecule detector and a distributor, and individually activating each of the electrodes of the multielectrode collector according to a signal coming from the molecule detector.

In an embodiment of the process, the macromolecules can be made to move towards a semipermeable wall in the multielectrode collector.

In the device for carrying out the process, the line leaving the separation unit containing the support leads via a molecule detector into a distributor, which in turn is linked via lines to a multielectrode collector; an electrode, which can be switched according to the detector signal, is associated with each line in the multielectrode collector. The counterelectrode is arranged in the inlet of the separation unit. A semipermeable wall can be arranged in the multielectrode collector.

The process and the device enable the components separated in the support to be obtained quantitatively, i.e. without losses of yield, in an easy manner. All that is required is a detector, adapted to the particular problem, for individually directing the current flow in the distributor. The semipermeable wall makes it possible to concentrate the components in the electrolyte. This process is preferably used for the separation of water-insoluble proteins, e.g. glycoproteins, membrane proteins, lipoproteins and fused proteins. The separation is efficient and takes place under mild conditions. The process is not restricted to the separation of proteins, however, and is equally suitable for the separation of other charged or strongly polarizable macromolecules such as DNA, RNA, antibodies etc.

The process is illustrated in greater detail below with the aid of the Figure, which shows a flow chart.

A protein mixture of phosphorylase B, bovine serum albumin, ovalbumin, carboanhydrase, trypsin inhibitor from soybean and lysozyme from hen's egg-white is fed into the separation unit, consisting of an electrolyte (buffer) reservoir 1 with counterelectrode 2 and a glass or plastic separation column 3, and separated electrophoretically into sharp discrete bands of the individual proteins. The separation column 3 is packed with a support consisting of a hydrophilic low-molecular to high-molecular polymeric separation medium such as acrylamide/N,N'-methylene-bis-acrylamide copolymer of varying concentration and pore size, or agarose. By a kind of carrier-free electrophoresis, the proteins separated in the separation column 3 pass via a line 4, filled with electrolyte, into a molecule detector 5 which can consist e.g. of a UV-visible detector with micro measuring cell and in-circuit chart recorder and/or integrator or data plotting station 10. Fluorescence detectors or radioactivity detectors are also suitable as molecule detectors. The proteins detected in the molecule detector 5 pass via a line 12 into a distributor 6 which is linked via lines 7 to individual containers 8 of a multielectrode collector 13. Semipermeable walls 15, such as dialysis membranes, can be arranged in the containers 8, but the latter can also be bounded by such walls. The individual containers 8 are arranged in an electrolyte (buffer) reservoir 9 and are each provided with an electrode 14. The electrodes 14 are switched according to the respective molecule detector signal being processed, which ensures that only a very specific protein passes into an individual container 8, where it is concentrated. The purpose of the electrolyte (buffer) reservoir is to prevent the electrolyte from becoming exhausted. To detach the proteins from the semipermeable wall, the polarity of the current flow in the device can be reversed for a short period. The power unit for supplying the current is denoted by 11.

What is claimed is:

1. A method for electrophoretically separating, purifying and concentrating charged or polarized macromolecules, the method comprising the steps of:
   separating the macromolecules in a separation column, the separation column containing a support medium;
   migrating the separated macromolecules out of the support medium using electrophoretic current;
   feeding the separated macromolecules into a molecule detector;
   feeding the separated macromolecules from the molecule detector into a distributor; and
   collecting the separated macromolecules in a multielectrode collector, each of the electrodes of said collector being individually activatable by a signal from the molecule detector.

2. A method as set for the in claim 1, wherein the support medium is a bar gel.

3. A method as set forth in claim 1, wherein the support medium is a slab.

4. A method as set forth in claim 1, wherein the multielectrode collector includes at least one semipermeable wall, the method further comprising the step of moving the macromolecules in the collector toward said at least one semipermeable wall.

5. A device for electrophoretic separation, purification, and concentration of charged or polarized macromolecules from a mixture of macromolecules, the device comprising:
- a separation unit for containing a separation medium, said separation unit having an inlet and a counterelectrode disposed therein;
- a molecule detector;
- a distributor;
- a multielectrode collector;
- means for flow communicating said separation unit with said molecule detector;
- means for flow communicating said molecular detector with said distributor;
- means for flow communicating said distributor with said multielectrode collector; and
- means for transmitting a signal from said molecular detector to said multielectrode collector, said signal for individually activating the electrodes of said multielectrode collector.

6. A device as set forth in claim 5, wherein said multielectrode collector includes an electrolyte reservoir and individual containers arranged in said electrolyte reservoir, said containers having semipermeable walls.

7. A device as set forth in claim 5, wherein said semipermeable walls include dialysis membranes.

8. A device as claimed in claim 7, wherein the molecular detector includes a chart recorder.

9. A device as set forth in claim 5, wherein the molecule detector includes a UV-visible detector and a micromeasuring cell.

10. A device as set forth in claim 5, wherein the molecular detector includes a fluorescence detector.

11. A device as set forth in claim 5, wherein the molecule detector includes a radioactivity detector.

12. A device as claimed in claim 5, wherein the means for flow communicating the separation unit with the molecular detector includes a line filled with electrolyte.

13. A device as claimed in claim 5, wherein said means for flow communicating said distributor with said multielectrode collector includes a plurality of conduits, each conduit corresponding to a separate electrode of said multielectrode collector.

* * * * *

UNITED STATES PATENT AND TRADEMARK OFFICE
CERTIFICATE OF CORRECTION

PATENT NO. : 4,948,481

DATED : August 14, 1990

INVENTOR(S) : Stefan MULLNER

It is certified that error appears in the above-identified patent and that said Letters Patent is hereby corrected as shown below:

Claim 2, column 2, line 62, delete "for the" and insert --forth--.

Signed and Sealed this

Seventeenth Day of November, 1992

*Attest:*

DOUGLAS B. COMER

*Attesting Officer*    *Acting Commissioner of Patents and Trademarks*